United States Patent
Arakita et al.

(10) Patent No.: US 9,690,902 B2
(45) Date of Patent: Jun. 27, 2017

(54) IMAGE OBSERVATION APPARATUS TO DISPLAY MEDICAL IMAGES FROM A PLURALITY OF APPARATUS TYPES

(71) Applicant: Toshiba Medical Systems Corporation, Otawara-shi (JP)

(72) Inventors: Kazumasa Arakita, Nasushiobara (JP); Satoshi Wakai, Nasushiobara (JP); Kota Aoyagi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 34 days.

(21) Appl. No.: 14/729,246

(22) Filed: Jun. 3, 2015

(65) Prior Publication Data
US 2015/0269315 A1 Sep. 24, 2015

Related U.S. Application Data

(63) Continuation of application No. PCT/JP2013/084747, filed on Dec. 25, 2013.

(30) Foreign Application Priority Data

Dec. 25, 2012 (JP) ................. 2012-281404

(51) Int. Cl.
*G06K 9/00* (2006.01)
*G06F 19/00* (2011.01)
(Continued)

(52) U.S. Cl.
CPC .......... *G06F 19/321* (2013.01); *A61B 5/0035* (2013.01); *A61B 5/743* (2013.01);
(Continued)

(58) Field of Classification Search
None
See application file for complete search history.

(56) References Cited

U.S. PATENT DOCUMENTS

2005/0107689 A1* 5/2005 Sasano ................. A61B 6/032
600/425
2007/0250855 A1* 10/2007 Quinn-Jacobs ... G06F 17/30696
725/35

(Continued)

FOREIGN PATENT DOCUMENTS

JP 2006-006671 A 1/2006
JP 2008-192044 A 8/2008

(Continued)

OTHER PUBLICATIONS

International Search Report issued Jan. 28, 2014 for PCT/JP2013/084747 filed on Dec. 25, 2013 with English Translation.

(Continued)

*Primary Examiner* — Tahmina Ansari
(74) *Attorney, Agent, or Firm* — Oblon, McClelland, Maier & Neustadt, L.L.P.

(57) ABSTRACT

The extraction unit extracts a plurality of medical images as a list display target from an image storage unit storing a plurality of medical images and an plurality of apparatus types in association with each other. The list generation unit generates a list in which a plurality of reduced images respectively corresponding to the plurality of extracted medical images are arranged. The plurality of reduced images are arranged for each apparatus type in the list, and the list clearly indicates a reduced image corresponding to a candidate image of the plurality of extracted medical images that is more likely to be used. The display displays the generated list.

18 Claims, 11 Drawing Sheets

(51) Int. Cl.
*A61B 5/00* (2006.01)
*G06T 7/00* (2017.01)
*G06T 11/60* (2006.01)
*A61B 5/055* (2006.01)
*A61B 5/044* (2006.01)

(52) U.S. Cl.
CPC .......... *A61B 5/7425* (2013.01); *A61B 5/7445* (2013.01); *G06T 7/0016* (2013.01); *G06T 11/60* (2013.01); *A61B 5/002* (2013.01); *A61B 5/0013* (2013.01); *A61B 5/044* (2013.01); *A61B 5/055* (2013.01); *G06T 2207/30004* (2013.01); *G06T 2210/41* (2013.01)

(56) References Cited

U.S. PATENT DOCUMENTS

2010/0232661 A1* 9/2010 Hisanaga .............. G06F 19/321
                                                    382/128
2012/0278359 A1* 11/2012 Igarashi ................ G06F 19/321
                                                    707/769
2015/0269315 A1* 9/2015 Arakita ................. G06F 19/321
                                                    382/131

FOREIGN PATENT DOCUMENTS

| JP | 2010-211749 A | 9/2010 |
|---|---|---|
| JP | 2011-024688 A | 2/2011 |
| JP | 2012-230672 A | 11/2012 |
| JP | 2013-114485 A | 6/2013 |
| JP | 2013-228968 A | 11/2013 |

OTHER PUBLICATIONS

Written Opinion issued Jan. 28, 2014 for PCT/JP2013/084747 filed on Dec. 25, 2013.

* cited by examiner

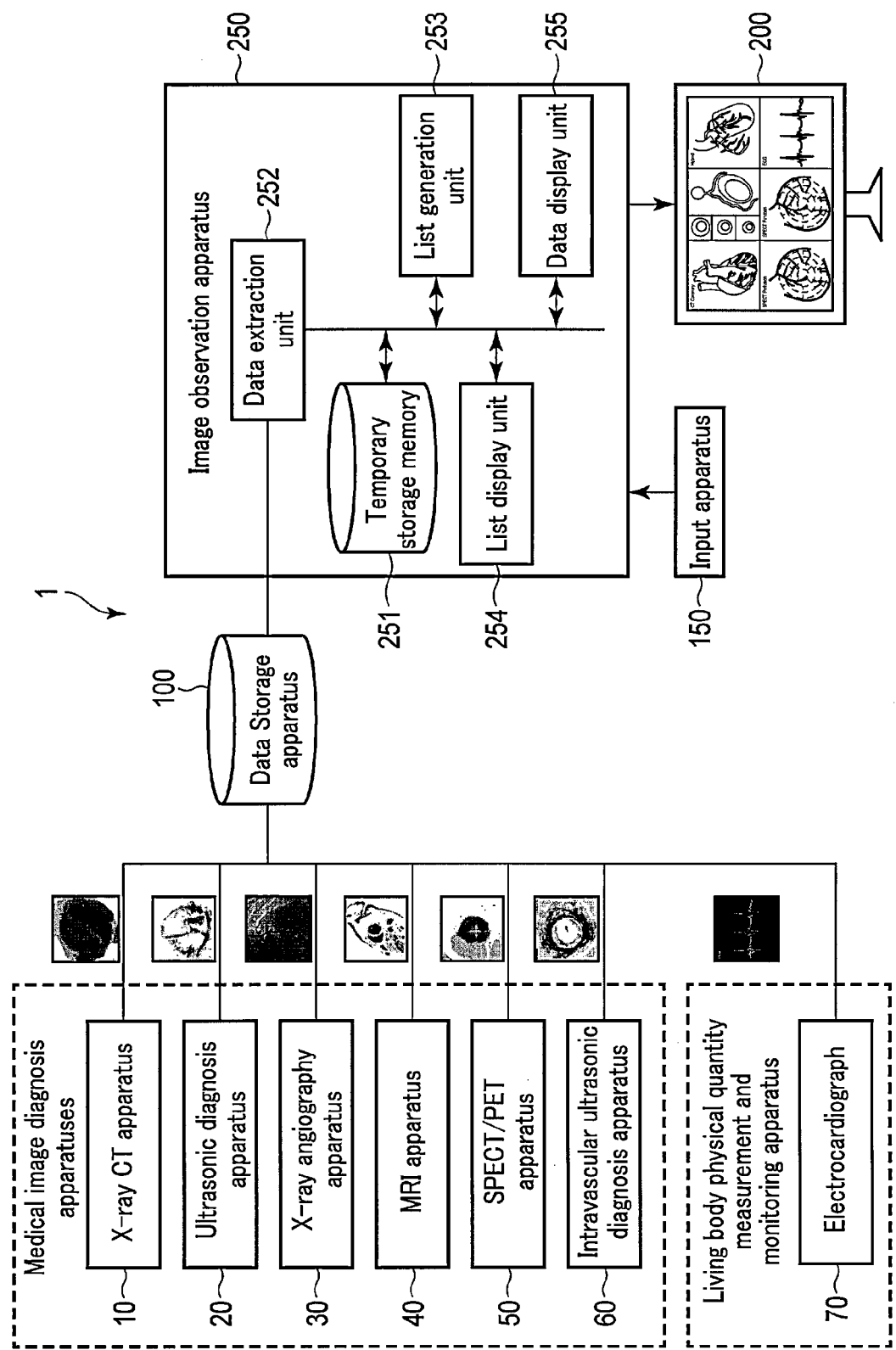
F I G. 1

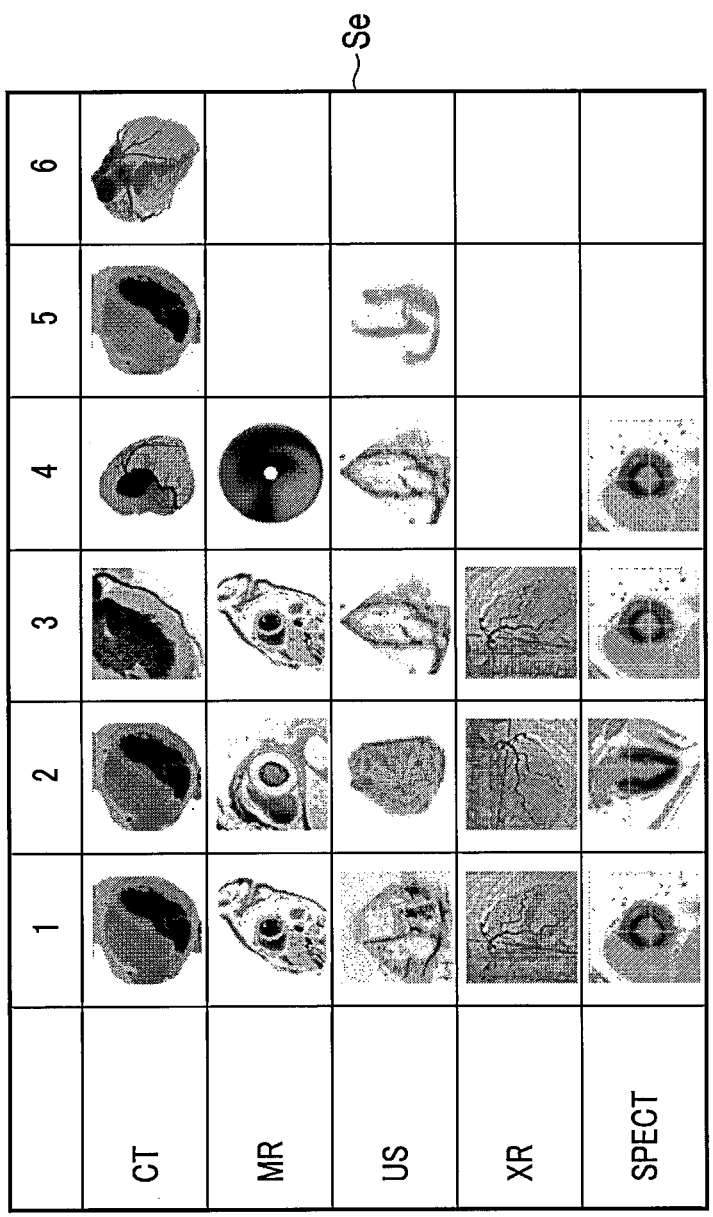
F I G. 2

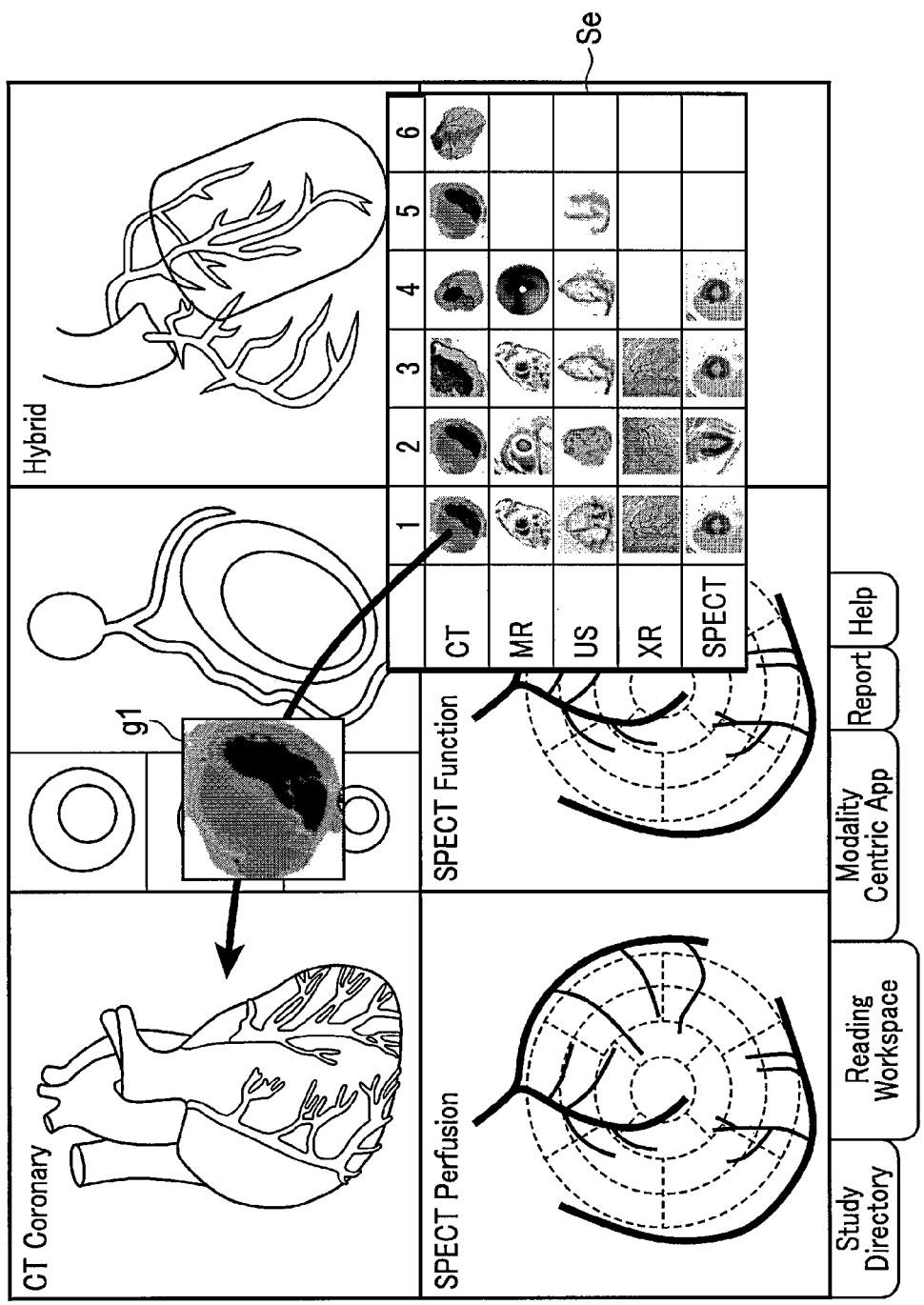
F I G. 3

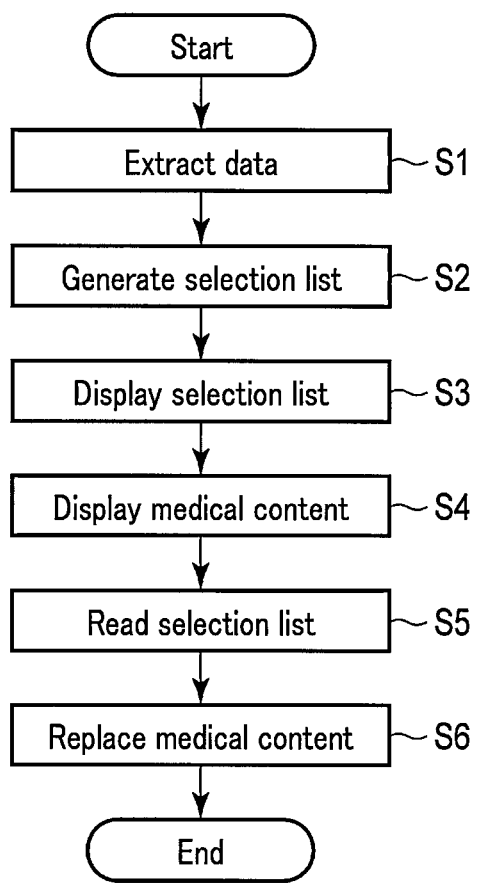
F I G. 4

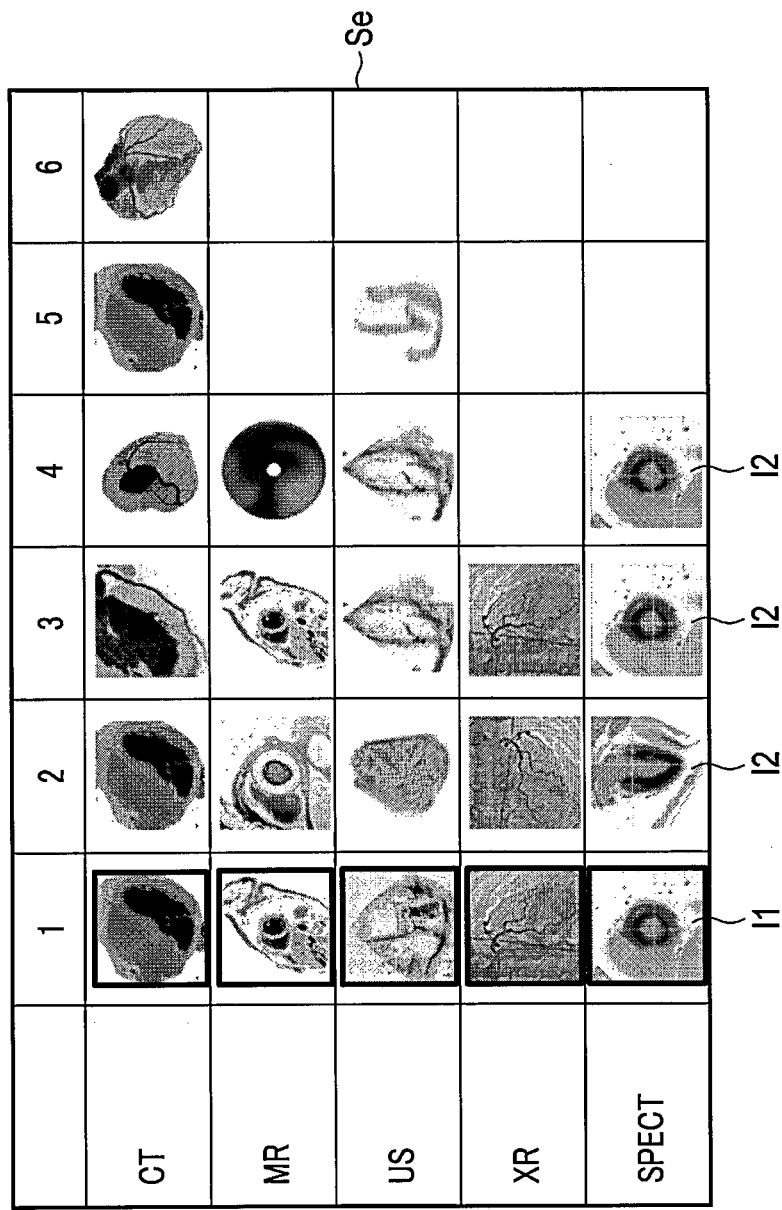
F I G. 6

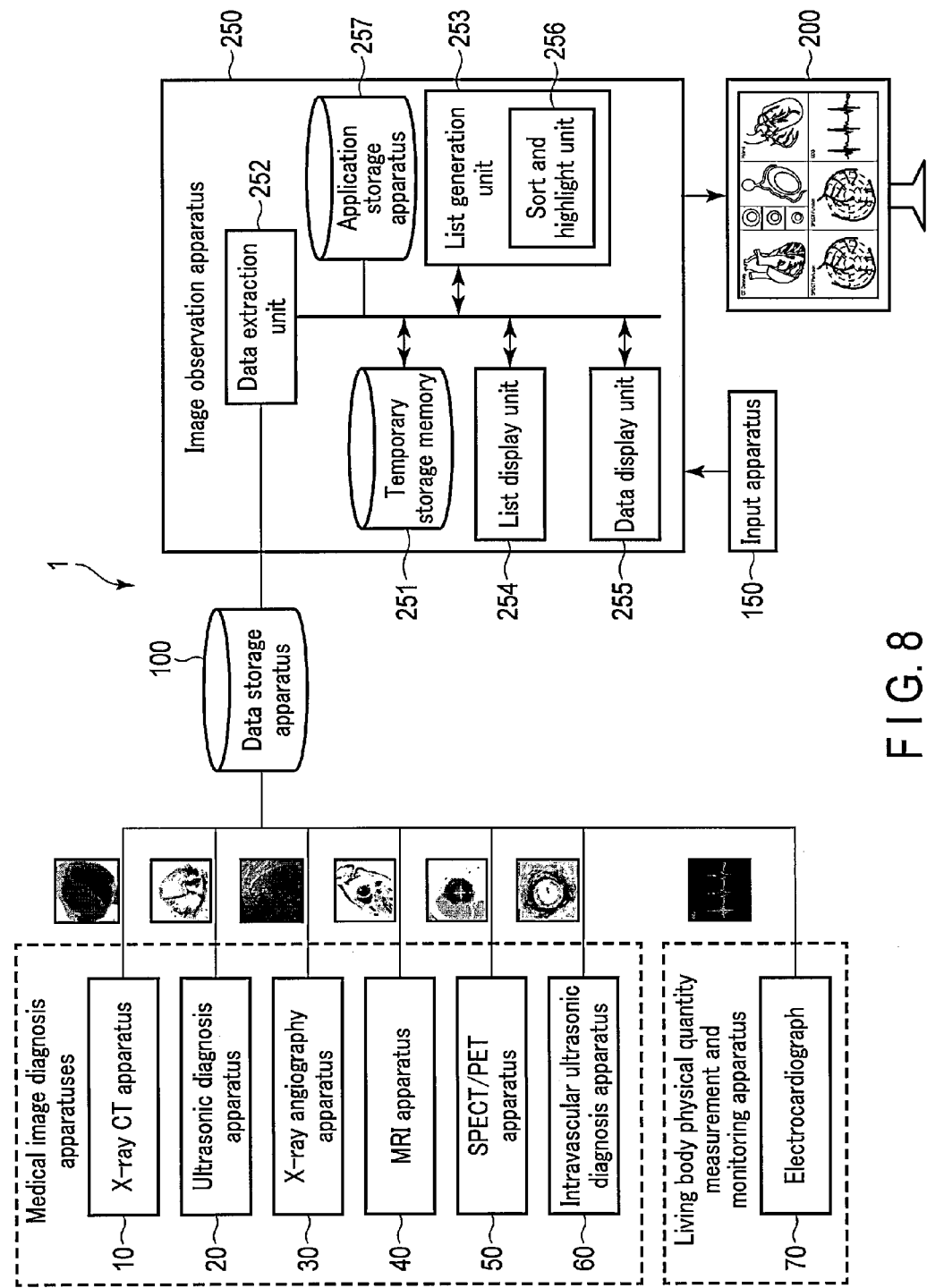
F I G. 8

| ID | Application name | Selection condition |
|---|---|---|
| 1 | Heart analysis program | Condition 1 |
| 2 | Brain analysis program | Condition 2 |
| 3 | Large intestine analysis program | Condition 3 |
| ⋮ | ⋮ | ⋮ |

| ID | Disease name | Selection condition |
|---|---|---|
| 1 | Ischemic heart diseases | Condition1 |
| 2 | Brain infarct | Condition2 |
| 3 | Pneumonia | Condition3 |
| ⋮ | ⋮ | ⋮ |

IMAGE OBSERVATION APPARATUS TO DISPLAY MEDICAL IMAGES FROM A PLURALITY OF APPARATUS TYPES

CROSS-REFERENCE TO RELATED APPLICATIONS

This application is a Continuation application of PCT Application No. PCT/JP2013/084747, filed Dec. 25, 2013 and based upon and claims the benefit of priority from the Japanese Patent Application No. 2012-281404, filed Dec. 25, 2012, the entire contents of which are incorporated herein by reference.

FIELD

Embodiment described herein relate generally to an image observation apparatus, an image observation method, and a computer-readable recording medium.

BACKGROUND

In medical image diagnosis, various kinds of image diagnosis apparatuses such as an X-ray CT (Computed Tomography) apparatus, an ultrasonic diagnosis apparatus, an MRI (Magnetic Resonance Imaging) apparatus, an X-ray angiography apparatus, and a SPECT/PET apparatus are used depending on the purposes of diagnosis. Hereinafter, an image diagnosis apparatus may be referred to as a modality.

In general, data of multiple types of medical images acquired by multiple modalities are transmitted to, for example, an image observation apparatus in a PACS (Picture Archiving and Communication System). In the image observation apparatus, an image viewer for displaying a medical image has already been introduced in advance. When the image observation apparatus receives data of a medical image, the image observation apparatus displays the received medical image on a screen of a monitor with an image viewer. At this occasion, in order for a user to be able to totally observe a morphological image and a functional image and compare and observe an examination image in the past and a current examination image, an image observation apparatus preferably displays multiple types of medical images on a screen at a time.

For this reason, in recent years, a multi-modality function has been introduced into an image observation apparatus in order to be able to display multiple types of medical images on a screen at a time. In this image observation apparatus, the image display area of the monitor is divided into multiple areas, and each of multiple types of medical images is displayed in each area. A user can select any medical image displayed in each area by referring to the image list. In this case, the image list means a list of all the medical images received by the image observation apparatus. The image list is displayed on the screen in a selection process of a medical image displayed in each area.

However, the image observation apparatus explained above has a drawback in that the user is unable to perform, in parallel, the image selection process for selecting image data displayed in each area from the image list, and the image verification process for precisely examining an image displayed in each area. More specifically, the image observation apparatus explained above has a drawback in that the image observation apparatus is unable to display an image list and a desired image in areas on the screen at a time, and needs to switch the screen on every such occasion, which is therefore cumbersome.

BRIEF DESCRIPTION OF THE DRAWING

FIG. 1 is a schematic diagram illustrating an example of configuration of a medical image display system including an image observation apparatus according to a first embodiment.

FIG. 2 is a schematic diagram illustrating an example of a selection list generated by the image observation apparatus according to the first embodiment.

FIG. 3 is a schematic diagram illustrating an example of process from when desired data are selected from a selection list generated by the image observation apparatus according to the first embodiment to when the data are displayed in a display area of a monitor.

FIG. 4 is a flowchart illustrating an example of operation of the image observation apparatus according to the first embodiment.

FIG. 6 is a schematic diagram illustrating an example of a selection list when sort and highlight are executed by the image observation apparatus according to the second embodiment.

FIG. 8 is a figure illustrating an example of configuration of a medical image display system including an image observation apparatus according to a third embodiment.

DETAILED DESCRIPTION

Figure 5:
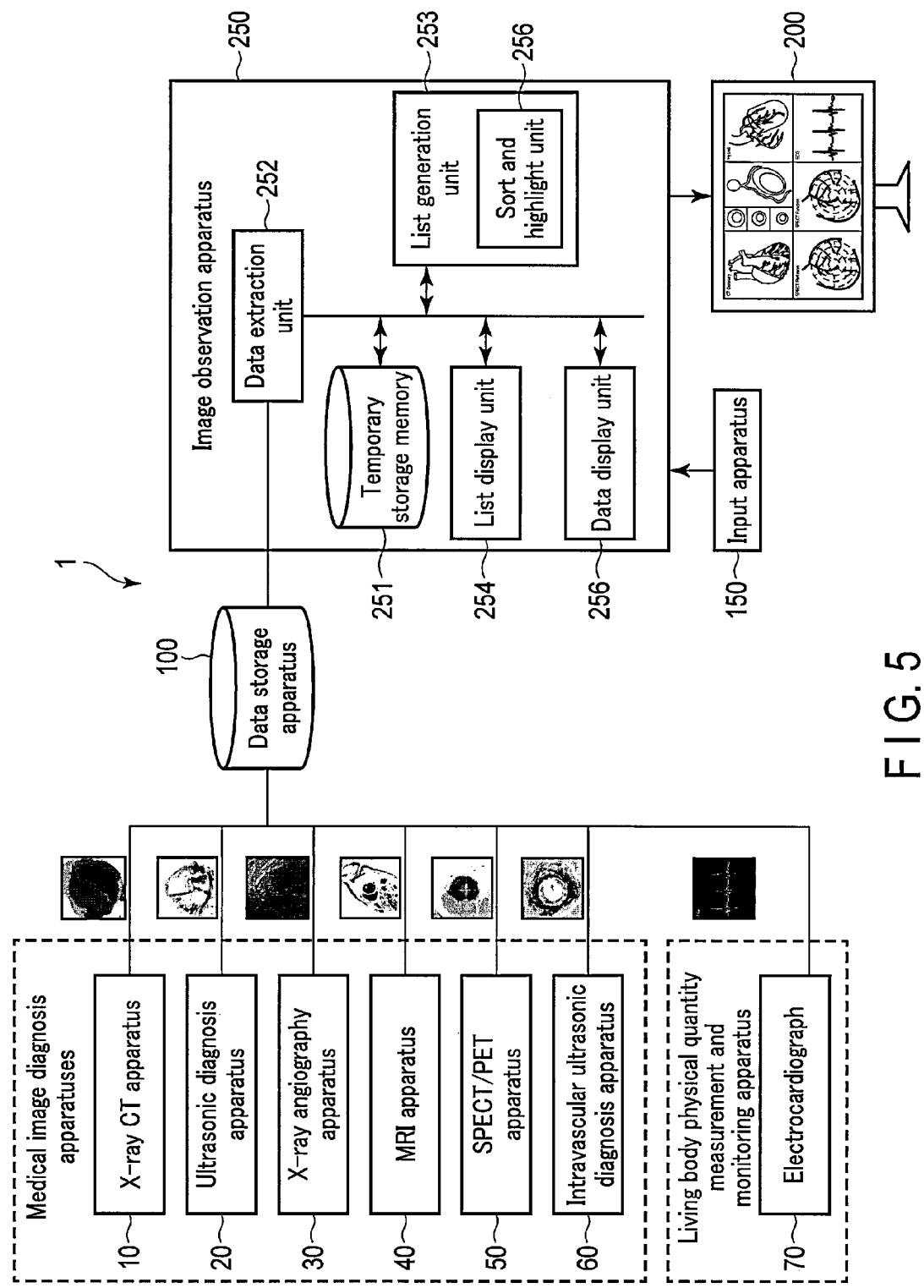
FIG. 5 is a schematic diagram illustrating an example of configuration of a medical image display system including an image observation apparatus according to a second embodiment.

In general, according to one embodiment, an image observation apparatus includes an extraction unit, a list generation unit, and display. The extraction unit extracts a plurality of medical images as a list display target from an image storage unit storing a plurality of medical images and an plurality of apparatus types in association with each other. The list generation unit generates a list in which a plurality of reduced images respectively corresponding to the plurality of extracted medical images are arranged. The plurality of reduced images are arranged for each apparatus type in the list, and the list clearly indicates a reduced image corresponding to a candidate image of the plurality of extracted medical images that is more likely to be used. The display displays the generated list. An image observation apparatus and a program thereof according to each embodiment will be hereinafter explained with reference to drawings. It should be noted that the following image observation apparatus can be implemented as either a hardware configuration or a combination of hardware resources and software.

Software having a combined configuration is installed to a computer from a recording medium or a network in advance, and a program is used to cause the computer to achieve each function of the image observation apparatus.

First Embodiment

FIG. 1 is a schematic diagram illustrating an example of configuration of a medical image display system including an image observation apparatus according to the first embodiment. FIG. 2 is a schematic diagram illustrating an example of a selection list generated by the image observation apparatus according to the embodiment. FIG. 3 is a schematic diagram illustrating an example of process from when desired data are selected from a selection list generated by the image observation apparatus according to the embodiment to when the data are displayed in a display area of a monitor.

A medical image display system 1 as shown in FIG. 1 includes multiple medical devices 10, 20, . . . , 70, a data storage apparatus 100, an input apparatus 150, a monitor 200, and an image observation apparatus 250. The medical devices 10 to 70 and the data storage apparatus 100 are connected to be able to communicate with each other, and the data storage apparatus 100 and the image observation apparatus 250 are connected to be able to communicate with each other. In the explanation below, the functions of the apparatuses 10 to 70, 100, 150, 200, 250 will be explained in details.

The medical devices 10 to 70 are medical image diagnosis apparatuses and living body physical quantity measurement and monitoring apparatuses, and, for example, as shown in FIG. 1, the medical devices 10 to 70 are an X-ray CT apparatus 10, an ultrasonic diagnosis apparatus 20, an X-ray angiography apparatus 30, an MRI apparatus 40, a SPECT/PET apparatus 50, an intravascular ultrasonic diagnosis apparatus (IVUS: intravascular ultrasound) 60, an electrocardiograph 70, and the like. In the present embodiment, the X-ray CT apparatus 10, the ultrasonic diagnosis apparatus 20, the X-ray angiography apparatus 30, the MRI apparatus 40, the SPECT/PET apparatus 50, the intravascular ultrasonic diagnosis apparatus 60, and the electrocardiograph 70 are shown as examples of typical medical image diagnosis apparatuses and living body physical quantity measurement and monitoring apparatuses, but the medical image diagnosis apparatuses and the living body physical quantity measurement and monitoring apparatuses are not limited thereto. As long as they are medical image diagnosis apparatuses and living body physical quantity measurement and monitoring apparatuses, they can be applied to medical devices constituting the medical image display system 1 as necessary.

The data storage apparatus 100 is a storage apparatus storing data of multiple types of medical images acquired by the medical image diagnosis apparatuses 10 to 60 and data of measurement results measured by the living body physical quantity measurement and monitoring apparatus 70. Hereinafter the medical images and the measurement results are collectively referred to as medical contents.

Data of each medical image are managed in a format of a so-called DICOM (Digital Imaging Communications and Medicine) image file which is the standard specification in image examination field. A DICOM header (which may be hereinafter also referred to as additional information) is associated with data of a medical image. The DICOM header includes at least a patient ID for identifying a patient. The DICOM header may include not only the patient ID but also feature information indicating the feature of a medical image. More specifically, the feature information includes a modality ID for identifying the apparatus type of each of the medical image diagnosis apparatuses 10 to 60, a imaging date, a imaging portion, image type information indicating whether the image is a morphological image or a functional image, contrast agent presence/absence information indicating presence/absence of a contrast agent during imaging, and electrocardiogram gate information indicating whether the imaging is using electrocardiogram gate method. In addition, the feature information includes, i.e., analysis presence/absence information indicating presence/absence of analysis performed by each of the medical image diagnosis apparatuses 10 to 60.

Data of the measurement result include the same information as the DICOM header explained above. In the present embodiment, the feature information includes various kinds of information explained above. However, various kinds of information included in the feature information are not limited thereto.

The data storage apparatus 100 functions as a server apparatus having a communication unit and the like, not shown, capable of communicating with each of the medical devices 10 to 70 and the image observation apparatus 250. Further, in the present embodiment, the data storage apparatus 100 is considered to be located outside of the image observation apparatus 250, but the present embodiment is not limited thereto. The data storage apparatus 100 may be implemented on the image observation apparatus 250 instead of the temporary storage memory 251 in the image observation apparatus 250 explained below.

The input apparatus 150 is an input interface executing various kinds of input processing on the image observation apparatus 250 in response to user's operation. More specifically, the input apparatus 150 is a mouse, a keyboard, a touch panel, and the like. Various kinds of input processing correspond to input processing of the patient ID, input of a list display request, and the like.

The monitor 200 is a display apparatus displaying medical images and measurement results extracted from the data storage apparatus 100 by the image observation apparatus 250. It should be noted that the monitor 200 has a function of dividing a single display area into multiple small areas in order to display multiple medical images and measurement results on the same screen. The number of small areas may be set to any value by the user with the input apparatus 150.

In this case, as shown in FIG. 1, the image observation apparatus 250 includes a temporary storage memory 251, a data extraction unit 252, a list generation unit 253, a list display unit 254, and a data display unit 255. The functions of the units 251 to 255 constituting the image observation apparatus 250 will be hereinafter explained in details.

The temporary storage memory 251 is a storage apparatus for temporarily storing medical contents extracted by the data extraction unit 252 explained later (data of medical images and measurement results). It should be noted that various kinds of medical content stored in the temporary storage memory 251 may be deleted from the temporary storage memory 251 with every desired period of time in order to allow the image observation apparatus 250 to perform operation smoothly.

The data extraction unit 252 extracts multiple medical contents of the list display target from multiple medical contents stored in the data storage apparatus 100. For example, the list display target is designated by the patient ID. In this case, the data extraction unit 252 extracts, from the data storage apparatus 100, data of medical images and measurement results associated with the patient ID which is input with the input apparatus 150. The data extraction unit 252 writes the extracted data of medical images and measurement results to the temporary storage memory 251.

In the above explanation, the list display target is designated by the patient ID, but the present embodiment is not limited thereto. For example, the list display target may be obtained by extracting various kinds of medical contents in accordance with input of any given information in the DICOM header (for example, a imaging date, a measurement date, and the like). In the present embodiment, the data extraction unit 252 extracted various kinds of medical contents from the data storage apparatus 100, but the present embodiment is not limited thereto. For example, the data extraction unit 252 may directly extract various kinds of medical contents from each of the medical devices 10 to 70.

The list generation unit 253 generates a selection list (MM-Selector) having multiple reduced images (thumbnail image) arranged to respectively correspond to multiple medical contents stored in the temporary storage memory 251, i.e., multiple medical contents extracted by the data extraction unit 252. In the selection list, multiple thumbnail images are arranged according to the apparatus type (modality), and the selection list clearly indicates thumbnail images corresponding to some of the extracted medical contents that are more likely to be used. In the selection list, multiple thumbnail images respectively corresponding to multiple medical contents are arranged in a matrix form. By observing the selection list, the user can see multiple medical contents as a list. The list generation unit 253 generates multiple thumbnail images respectively corresponding to multiple medical contents by arranging the multiple thumbnail images in accordance with a conformity result indicating that multiple DICOM headers respectively corresponding to the multiple medical contents are in conformity with the selection condition. The selection condition is a condition for defining the vertical axis and the horizontal axis of the selection list. The selection condition can be set to any condition by the user with the input apparatus 150. For example, in a selection list Se as shown in FIG. 2, the vertical axis indicates the modality ID (apparatus type), and the horizontal axis indicates an image series. In this case, the list generation unit 253 classifies the multiple medical contents into apparatus types, and further arranges the thumbnails corresponding to the medical contents classified into apparatus types in accordance with image series. In FIG. 2, the apparatus types include a CT (X-ray CT apparatus), an MR (MRI apparatus), a US (ultrasonic diagnosis apparatus), an XR (X-ray angiography apparatus), and a SPECT (SPECT apparatus). Multiple thumbnail images respectively corresponding to multiple medical images of each apparatus type are arranged in the order of the series number.

In the present embodiment, the list generation unit 253 is assumed to generate the selection list in the thumbnail format like the selection list Se as shown in FIG. 2. However, the format of the selection list generated by the list generation unit 253 is not limited thereto. The thumbnail images in the selection list Se as shown in FIG. 2 may be two-dimensional images, or three-dimensional images. For example, in the selection list of the thumbnail format using three-dimensional images, a function may be further added to display another three-dimensional image by overlaying the cursor of the input apparatus 150 (for example, mouse and the like) to the thumbnail image. Further, in the present embodiment, the list generation unit 253 is assumed to generate a selection showing a list of data of medical images and measurement results stored in the temporary storage memory 251. However, for example, when the temporary storage memory 251 stores only the data of the medical images, the list generation unit 253 may generate a selection list showing a list of data of the medical images.

The list display unit 254 displays a selection list generated by the list generation unit 253 on the monitor. More specifically, the list display unit 254 displays the selection list overlaid on the display area of the application program for image precise examination (Reading-Workspace). For example, when the list display unit 254 receives a display request of a selection list from the input apparatus 150, for example, as shown in FIG. 3, the list display unit displays the selection list Se overlaid on the display area (Reading-Workspace). It should be noted that the display area (Reading-Workspace) is divided, as shown in FIG. 3, into multiple small areas for displaying medical images or measurement results for image precise examination.

When any one of multiple thumbnail images in the selection list displayed on the monitor 200 is selected with the input apparatus 150, the data display unit 255 displays the medical image or the measurement result corresponding to the selected thumbnail image in any one of the small areas of the display area (Reading-Workspace). In other words, the selection list Se as well as the medical images and the measurement results displayed in the display area (Reading-workspace) are displayed in the display area of the monitor 200.

It should be noted that there are multiple methods for displaying various kinds of medical contents in the selection list in each small area of the display area (Reading-Workspace). Examples of such methods include, as shown in FIG. 3, drag and drop (D&D). In this case, the user uses the input apparatus 150 to drag and drop the thumbnail image of any given medical content in the selection list to one of the multiple small areas where it is to be displayed. The data display unit 255 inserts the medical content corresponding to drag and drop thumbnail image into the small area of the moving destination. Another method is a click. In this case, the user uses the input apparatus 150 to select the thumbnail image corresponding to the medical content to be displayed in the display area (Reading-Workspace) from among multiple thumbnail images displayed in the selection list and double clicks the thumbnail image. The data display unit 255 inserts the medical content corresponding to the double clicked thumbnail image into any one of the multiple small areas. For each disease name, various kinds of medical contents displayed on the monitor 200 may be set in advance, so that various kinds of medical contents may be displayed on the monitor 200 in accordance an input of a disease name with the input apparatus 150.

Subsequently, an example of operation of the image observation apparatus 250 configured as described above will be explained with reference to the schematic diagrams of FIGS. 2 and 3 and the flowchart of FIG. 4.

First, when the data extraction unit 252 receives the input of the patient ID inputted by the input apparatus 150, the data extraction unit 252 extracts data of the medical images and the measurement result associated with the patient ID of which input has been received from the data storage apparatus 100 (step S1). The data extraction unit 252 writes data of the extracted medical images and the measurement results to the temporary storage memory 251.

Subsequently, the list generation unit 253 generates a selection list according to a desired selection condition based on the medical images and the measurement results stored in the temporary storage memory 251 (step S2). In this case, as shown in FIG. 2, the list generation unit 253 generates a selection list Se in which the vertical axis indicates a modality ID and the horizontal axis indicates an image series. It should be noted that the selection list Se is written, as necessary, to a memory, not shown, by the list generation unit 253, and maintained in a readily readable state upon necessity.

Subsequently, when the list generation unit 253 generates the selection list Se, the list display unit 254 displays the selection list Se on the monitor 200 (step S3).

Subsequently, when the input apparatus 150 is used to select the thumbnail image of the medical image or the measurement result in the selection list Se, the data display unit 255 displays the medical image or the measurement result corresponding to the selected thumbnail image in any one of multiple small areas of the display area (Reading-Workspace) (step S4).

The processing in steps S1 to S4 explained above is an example of series of processing from when a desired medical content is extracted to when it is displayed on the monitor 200.

In this case, when the list display unit 254 receives a list display request via the input apparatus 150, the list display unit 254 displays the already generated selection list Se on the display area (Reading-Workspace). In other words, the list display unit 254 displays the medical image and the measurement result already displayed as well as the selection list Se in the small area of the display area (Reading-Workspace) (step S5).

Thereafter, when a thumbnail image in the selection list Se is selected with the input apparatus 150, the data display unit 255 displays the medical image or the measurement result corresponding to the selected thumbnail image in each small area (step S6). For example, as shown in FIG. 3, when a thumbnail image g1 in the selection list Se is selected, and the selected thumbnail image g1 is dragged and dropped to the upper left small area of the small areas divided into six the data display unit 255 displays the medical image corresponding to the selected thumbnail image instead of the medical content already displayed in the small area.

In the present embodiment, the case where the data storage apparatus 100 and a single image observation apparatus 250 are connected to be able to communicate with each other has been explained. Alternatively, the data storage apparatus 100 may be connected to multiple image observation apparatuses 250 to be able to communicate therewith. At this occasion, when any give image observation apparatus 250 displays a predetermined medical image on the monitor 200, the medical image portion in the selection list of another image observation apparatus 250 may have any given mark indicating that the any given image observation apparatus 250 is displaying the medical image on the monitor 200. (However, this is applicable only when the image observation apparatus is generating a selection list including the above predetermined medical image)

According to the first embodiment explained above, when an input of a list display request which is input with the input apparatus 150 is received, the already generated selection list is read from a memory and the like in accordance with the list display request of which input has been received, and thereafter, the list display unit 254 displays the selection list as well as the data of the medical images and the measurement results already displayed in display area of the monitor 200, and with this configuration, the selection list can be displayed on the screen of the monitor 200 at any time, and the user can change the data of the medical images and the measurement result with any given timing.

Second Embodiment

FIG. 5 is a schematic diagram illustrating an example of configuration of a medical image display system including an image observation apparatus according to the second embodiment. As shown in FIG. 5, a list generation unit 253 of the image observation apparatus according to the second embodiment includes a sort and highlight unit 256. FIG. 6 is a schematic diagram illustrating an example of a selection list when sort and highlight are executed by the image observation apparatus of FIG. 5. In the explanation below, constituent elements having substantially the same function as those of the first embodiment are denoted with the same reference numerals, and will be explained repeatedly only when necessary.

The sort and highlight unit 256 sorts multiple thumbnail images in the selection list so that thumbnail images corresponding to thumbnail images included in the selection list in conformity with a selection condition are given a higher order of priority than other thumbnail images. Alternatively, the sort and highlight unit 256 visually emphasizes (highlights) thumbnail images corresponding to medical images of multiple thumbnail images included in the selection list in conformity with a selection condition in such a manner that the thumbnail images are visually emphasized (highlighted) as compared with other thumbnail images. It should be noted that a user can configure whether the sort and highlight unit 256 executes any one of sorting, highlighting, or sorting and highlighting.

The selection condition is a condition for selecting multiple medical images of positioning target from among multiple medical contents extracted from the data extraction unit 252. In this case, the sort and highlight unit 256 determines whether one or more medical images satisfying selection condition (A) shown below and one or more medical images satisfying selection condition (B) shown below exists in the selection list or not in order to identify medical images that can be positioned. Then, the sort and highlight unit 256 sets medical images satisfying selection condition (A) and medical images satisfying selection condition (B) as medical images that are likely to be used (hereinafter referred to as candidate images). As shown in FIG. 6, the sort and highlight unit 256 sorts the selection list Se so that the thumbnail image I1 corresponding to the candidate image is given a higher order of priority than the thumbnail image I2 corresponding to another medical image not satisfying the selection condition. For example, in FIG. 6, the thumbnail image I1 is arranged from the left side with a higher order of priority than another thumbnail image I2. Therefore, the user can easily find the thumbnail image corresponding to the candidate image from the selection list. Alternatively, the sort and highlight unit 256 visually emphasizes the thumbnail image I1 corresponding to the candidate image as compared with the thumbnail image I2 corresponding to another medical image in the selection list Se. For example, in FIG. 6, the thumbnail image I1 emphasizes the frame. Therefore, the user can easily find the thumbnail image corresponding to the candidate image. It should be noted that the emphasis method is not limited to a mode of emphasizing the frame of the thumbnail image. It should be noted that the sort and highlight unit 256 may perform both of the sorting processing and the emphasis processing explained above.

Selection Condition (A)

The feature information in the additional information of a medical image includes the modality ID indicating the X-ray CT apparatus 10, the contrast agent presence/absence information indicating that a contrast agent is injected, and electrocardiogram gate information indicting that the imaging is done using an electrocardiogram gate method.

Selection Condition (B)

The feature information in the additional information of a medical image includes a modality ID indicating the SPECT/PET apparatus 50 and electrocardiogram gate information indicating that imaging is done using an electrocardiogram gate method.

In general, a medical image satisfying the condition (A) is a CT coronary shape image, and a satisfying the condition (B) is a functional image acquired by the SPECT/PET apparatus 50.

In the above case, it is indicted that one or more medical images satisfying the condition (A) and one or more medical images satisfying the condition (B) can be positioned. However, the present embodiment is not limited thereto. A medical image satisfying the condition (A) can also be positioned with medical images satisfying any one of the selection conditions of (C) and (D) shown below. The selection conditions of (C) and (D) are as follows.

Selection Condition (C)

The feature information in the additional information of a medical image includes a modality ID showing the ultrasonic diagnosis apparatus 20, and analysis presence/absence indicating image data analyzed by the ultrasonic diagnosis apparatus 20.

Selection Condition (D)

The feature information in the additional information of a medical image includes a modality ID indicating the MRI apparatus 40 and analysis presence/absence information indicating a medical image analyzed by the MRI apparatus 40.

In general, a medical image satisfying the selection condition (C) explained above is an ultrasonic functional image acquired by the ultrasonic diagnosis apparatus 20, and a medical image satisfying the selection condition (D) explained above is a perfusion image, a delayed enhancement image, and the like acquired by the MRI apparatus 40.

The selection condition is assumed to be a condition for selecting a medical image that can be positioned. However, the present embodiment is not limited thereto. For example, the selection condition may be configured to executing sort and highlight process based on whether a new parameter can be output or not by using two medical contents (for example, CFR that can be calculated by using a result of Stress/Rest and the like), a decision tree based on a guideline defined for each hospital or a generally-available guideline, a medical image currently displayed on the monitor 200, a modality manufacturer, an examination type, the number of times images are read, the number of times a report about a medical image is viewed, and the like.

Figure 7:
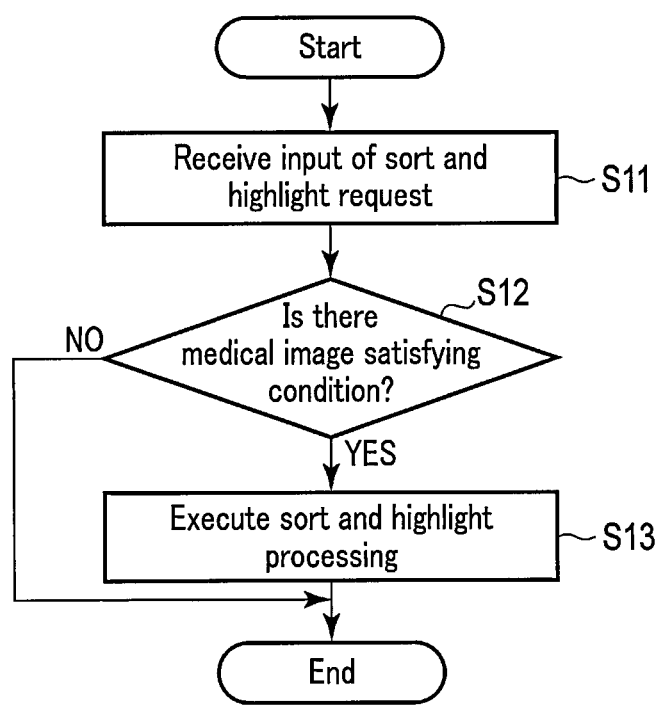
FIG. 7 is a flowchart illustrating an example of operation of the image observation apparatus according to the second embodiment.

Subsequently, an example of operation of the image observation apparatus 250 configured as described above will be explained with reference to a schematic diagram of FIG. 6 and a flowchart of FIG. 7.

First, the sort and highlight unit 256 receives a sort and highlight request via the input apparatus 150 in response to user's operation (step S11).

Subsequently, in response to the received sort and highlight request, the sort and highlight unit 256 determines whether, in the images corresponding to the thumbnail images in the selection list displayed on the list display unit 254, there are one or more medical images satisfying the condition (A) and one or more medical images satisfying any one of conditions (B) to (D) (step S12). When the result of the determination in the processing of step S12 is "not existing" (No in step S12), operation of the image observation apparatus 250 with regard to the example of operation is terminated.

When the result of the determination in the processing in step S12 is "existing" (Yes in step S12), the sort and highlight unit 256 sorts and/or highlights thumbnail images corresponding to one or more medical images satisfying the condition (A) and thumbnail images corresponding to one or more medical images satisfying any one of the conditions (B) to (D) (step S13).

In the selection list Se as shown in FIG. 6, all of the thumbnail images corresponding to the medical images satisfying the condition in the processing of step S12 are arranged at the left side, and the frames of the thumbnail images corresponding to the medical images are emphasized, but the contents of the sorting processing and the emphasis processing are not limited thereto, and the user can set in any manner using the input apparatus 150. For example, the sort and highlight unit 256 may sort all of the thumbnail images corresponding to the medical images satisfying the condition to be arranged at the right side. The sort and highlight unit 256 may change the emphasis method in accordance with the satisfied selection condition.

The image observation apparatus according to the second embodiment identifies, as a candidate image, a medical image that can be positioned, and clearly indicates a thumbnail image corresponding to the candidate image by sorting and/or highlighting the thumbnail image. The image observation apparatus according to the second embodiment can indicate a relationship between medical contents by clearly indicating the thumbnail image corresponding to the candidate image. Therefore, the image observation apparatus can present, to the user, which medical content is to be used to obtain an effective result.

In the above explanation, the list generation unit 253 clearly indicates the thumbnail image corresponding to the candidate image by sorting or highlighting. However, the present embodiment is not limited thereto. For example, the list generation unit 253 may arrange a list for only the thumbnail image corresponding to the candidate image. More specifically, when the user can reliably determine a candidate image, the list derivation unit 253 remains the thumbnail image corresponding to the candidate image in a selection list, and erases the other thumbnail images from the selection list. The case where the user can reliably determine a candidate image corresponds to, for example, a case where the number of candidate images is less than a predetermined number in each apparatus type. The predetermined number may be set to a number of thumbnail images that fit within the display range of the monitor 200 of the selection list, or may be set to any number that is set by the user with the input apparatus 150.

Third Embodiment

FIG. 8 is a schematic diagram illustrating an example of configuration of a medical system including an image observation apparatus according to the third embodiment. As shown in FIG. 8, the image observation apparatus according to the third embodiment further includes an application storage apparatus 257. In the explanation below, constituent elements having substantially the same function as those of the first and second embodiments are denoted with the same reference numerals, and will be explained repeatedly only when necessary.

The application storage apparatus 257 is a storage apparatus storing each of identifiers of multiple application programs with regard to image display in association with a selection condition for selecting a medical image that is more likely to be used. For example, the application storage apparatus 257 includes a table in which an identifier of an application program and a selection condition are associated with each other. Hereinafter, the table will be referred to as an application table. The identifier of the application program may be an ID, an application, and the like.

Figures 9, 10:
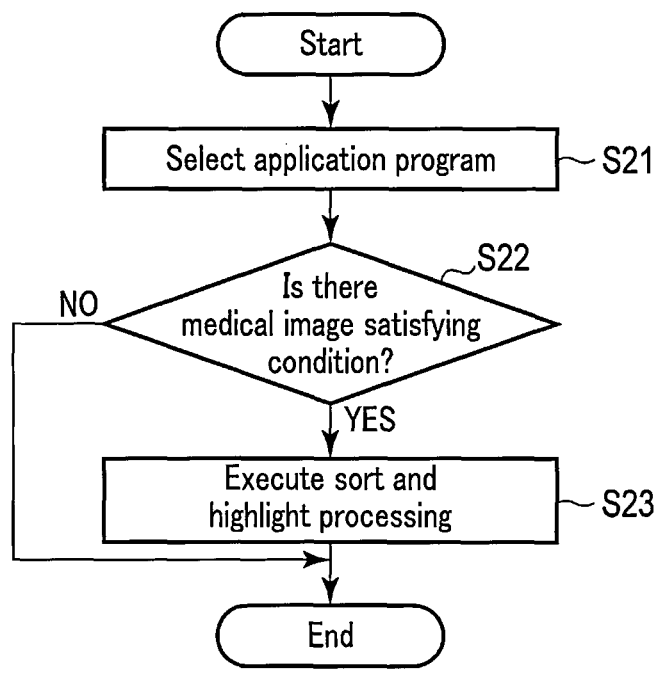
FIG. 9 is a figure illustrating an example of an application table stored in an application storage apparatus of FIG. 8.
FIG. 10 is a flowchart illustrating an example of operation of the image observation apparatus according to the third embodiment.

FIG. 9 is a figure illustrating an example of an application table. As shown in FIG. 9, in the application table, the ID is associated with an application name and a selection condition. For example, the application name of the application program of the ID1 is a "heart analysis program", and the selection condition is "condition 1". Likewise, the application name of the application program of the ID2 is "brain analysis program", and the selection condition is "condition 2", and the application name of the application program of the ID3 is "large intestine analysis program", and the selection condition is "condition 3". The selection condition according to the third embodiment is defined in, for example, a condition for selecting a medical image suitable for the application program. More specifically, the apparatus type suitable for imaging the analysis target of the application program (imaging portion). Therefore, the selection condition is a medical image generated by an apparatus of the same type as the apparatus type suitable for imaging the analysis target of the application program. More specifically in a case of the "heart analysis program" of the ID1, the condition 1 is, for example, "CT". It should be noted that the selection condition is not limited to the above condition, and, for example, the selection condition may be the selection condition described in the first embodiment or may be the selection condition described in the second embodiment. The contents of the selection condition can be set to any content by the user with the input apparatus 150.

Subsequently, an example of operation of the image observation apparatus 250 according to the third embodiment configured as described above will be explained with reference to the flowchart of FIG. 10.

First, the sort and highlight unit 256 receives a selection of the application program with the input apparatus 150 in response to user's operation (step S21). A display area for selecting an application program (hereinafter referred to as a selection window) is displayed by the list display unit 254 when, for example, a selection button provided on the selection list, not shown, is pressed down. The user uses the input apparatus 150 to select a desired application name from among multiple application names displayed in the selection window.

Subsequently, the sort and highlight unit 256 reads the selection condition associated in the application table with the selected application name, and determines whether a medical image satisfying the read selection condition exists in multiple medical images respectively corresponding to multiple thumbnail images displayed in the selection list (step S22). When the result of the determination of step S22 is "not existing" (No in step S22), operation of the image observation apparatus 250 with regard to the example of operation is terminated. For example, the sort and highlight unit 256 determines whether each DICOM header of the multiple medical images matches the selection condition or not. For example, in a case where "brain analysis program" is selected in step S21, and the selection condition of "brain analysis program" is "MR", the sort and highlight unit 256 refers the value of each apparatus type of multiple medical images, and identifies the medical image having the value "MR". The identified medical image is set in the candidate image.

When the result of the determination in the processing of step S22 is "existing" (Yes in step S22), the sort and highlight unit 256 executes sort and highlight processing on the thumbnail image corresponding to the medical image satisfying the selection condition read in step S22 (step S23). More specifically, the sort and highlight unit 256 arranges the thumbnail image corresponding to the candidate image at the left side with a higher order of precedence than the other thumbnail images, and visually emphasizes the thumbnail image corresponding to the candidate image in such a manner that it is more emphasized as compared with the other thumbnail images.

As described above, the image observation apparatus according to the third embodiment can clearly indicate the thumbnail image corresponding to the medical image suitable for the application program selected by the user in the selection list.

Fourth Embodiment

Figure 11:
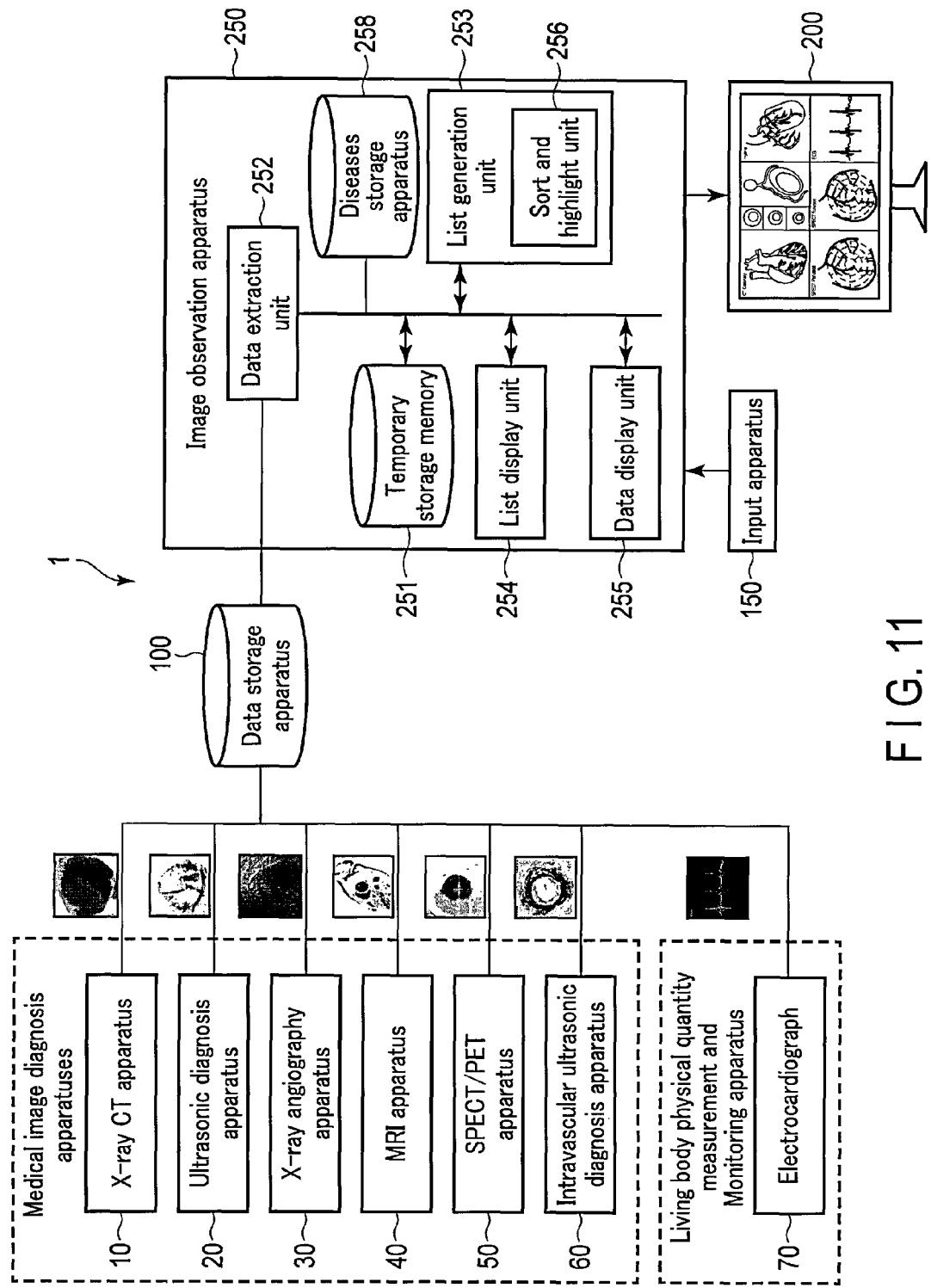
FIG. 11 is a figure illustrating an example of configuration of a medical image display system including an image observation apparatus according to a fourth embodiment.

FIG. 11 is a schematic diagram illustrating an example of configuration of a medical image display system including an image observation apparatus according to the fourth embodiment. As shown in FIG. 11, the image observation apparatus according to the fourth embodiment further includes a diseases storage apparatus 258. In the explanation below, constituent elements having substantially the same function as those of the first and second embodiments are denoted with the same reference numerals, and will be explained repeatedly only when necessary.

The diseases storage apparatus 258 is a storage apparatus for storing each identifier of multiple diseases in association with the selection condition a selection condition for selecting a medical content that is more likely to be used. For example, the diseases storage apparatus 258 includes a table in which an identifier of disease and a selection condition are associated with each other. Hereinafter, the table may be referred to as a diseases table. The ID and the disease name are preferably used as the identifiers of the diseases.

Figures 12, 13:
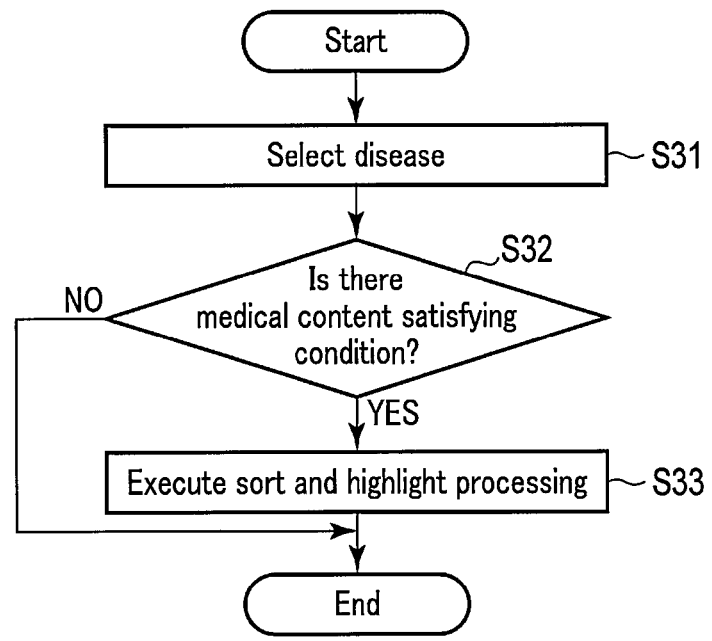
FIG. 12 is a figure illustrating an example of an application table stored in an application storage apparatus of FIG. 11.
FIG. 13 is a flowchart illustrating an example of operation of the image observation apparatus according to the fourth embodiment.

FIG. 12 is a figure illustrating an example of a diseases table. As shown in FIG. 12, in the diseases table, the identifier (ID) is associated with the disease name and the selection condition. For example, the disease name of the disease of ID1 is "ischemic heart diseases", and the selection condition is "condition 1". Likewise, the disease name of the disease of ID2 is "brain infarct", and the selection condition is "condition 2", and the disease name of the disease of ID3 is "pneumonia", and the selection condition is "condition 3". The selection condition according to the third embodiment is defined in, for example, a condition for selecting a medical content that is highly related to diagnosis of the diseases. More specifically, there are types of image types and measurement results and apparatus types suitable for diagnosis of diseases. For example, in the disease name is the "ischemic heart diseases", diagnosis is performed with a somewhat determined medical content such as medical contents such as a coronary analysis result of a CT and an original image of a CT, a cardiac muscle perfusion analysis result of SPECT, a coronary contrast agent examination result of angiography, and the like. Therefore, the selection condition is a medical content of a type and an image type of a measurement result and an apparatus type of the same type as a type and an image type of a measurement result and an apparatus type suitable for diagnosis of the diseases. More specifically, in a case of "ischemic heart diseases" of ID1, the condition 1 is, for example, "original image of CT", "coronary analysis result of CT", "cardiac muscle perfusion analysis result of SPECT", and "coronary contrast agent examination result of angiography". It should be noted that the selection condition is not limited to the above condition, and, for example, the selection condition may be the selection condition described in the first embodiment, or may be the selection condition described in the second embodiment. The contents of the selection condition can be set to any content by the user with the input apparatus 150.

Subsequently, an example of operation of the image observation apparatus 250 according to the fourth embodiment configured as described above will be explained with reference to the flowchart of FIG. 13.

First, the sort and highlight unit 256 receives a selection of the disease with the input apparatus 150 in response to user's operation (step S31). A display area for selecting a disease (hereinafter referred to as a selection window) is displayed by the list display unit 254 when, for example, a selection button provided on the selection list, not shown, is pressed down. The user uses the input apparatus 150 to select a desired application name from among multiple application names displayed in the selection window.

Subsequently, the sort and highlight unit 256 reads the selection condition associated in the application table with the selected disease name, and determines whether a medical content satisfying the read selection condition exists in multiple medical contents respectively corresponding to multiple thumbnail images displayed in the selection list (step S32). When the result of the determination in the processing of step S32 is "not existing" (No in step S32), operation of the image observation apparatus 250 with regard to the example of operation is terminated. For example, the sort and highlight unit 256 determines whether each DICOM header of the multiple medical images matches the selection condition or not. For example, in a case where "ischemic heart disease" is selected in step S31, and the selection condition of "brain analysis program" is "MR", the sort and highlight unit 256 refers the value of each DICOM header of multiple medical contents, and identifies the medical content having the value satisfying the selection condition of "ischemic heart diseases". The identified medical content is set in the candidate image.

When the result of the determination in the processing of step S32 is "existing" (Yes in step S32), the sort and highlight unit 256 executes sort and highlight processing on the thumbnail image corresponding to the medical content satisfying the selection condition read in step S32 (step S33). More specifically, the sort and highlight unit 256 arranges the thumbnail image corresponding to the medical content that is more likely to be used at the left side with a higher order of precedence than the other thumbnail images, and visually emphasizes the thumbnail image corresponding to the medical content that is more likely to be used in such a manner that it is more emphasized as compared with the other thumbnail images.

As described above, the image observation apparatus according to the fourth embodiment can clearly indicate a thumbnail image corresponding to a medical content suitable for a disease name selected by the user in the selection list.

Therefore, according to the present embodiment, the burden on the user with regard to image observation can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An image observation apparatus, comprising:
processing circuitry configured to
extract a plurality of medical images as a list display target from an image memory storing a plurality of images and a plurality of apparatus types in association with each other, and
generate a list in which a plurality of selectable reduced images respectively corresponding to the plurality of extracted medical images are arranged in a matrix having a vertical axis and a horizontal axis, the horizontal and vertical axes being defined by a condition input via an input apparatus, wherein the plurality of reduced images are arranged by each apparatus type in the list, and the list visually indicates a reduced image corresponding to a candidate image of the plurality of extracted medical images that is more likely to be used; and
a display configured to display the generated list.

2. The apparatus according to claim 1, further comprising an application memory to store an identifier of each of a plurality of application programs with regard to image display in association with a selection condition for the candidate image,
wherein the processing circuitry is further configured to identify the candidate image from among the plurality of extracted medical images based on a selection condition associated with an identifier of an application program selected by the user.

3. The apparatus according to claim 2, wherein the selection condition is for selecting a medical image suitable for observation with the application program.

4. The apparatus according to claim 1, wherein the display overlays the list on a display area of the application program for image precise examination.

5. The apparatus according to claim 4, wherein the display displays, in the display area, a medical image corresponding to a reduced image selected by a user from among the plurality of reduced images.

6. The apparatus according to claim 5, wherein the display area is divided into a plurality of areas, and
the display inserts a medical image corresponding to the selected reduced image into a particular area of the plurality of areas or an area designated by the user.

7. The apparatus according to claim 1, wherein the processing circuitry is further configured to collate additional information about the plurality of extracted medical images with a selection condition for selecting the candidate image, and set a medical image satisfying the selection condition to the candidate image.

8. The apparatus according to claim 7, wherein the processing circuitry is further configured to sort the plurality of reduced images in such a manner that a reduced image corresponding to the candidate image is given a higher order of precedence than other reduced images.

9. The apparatus according to claim 7, wherein the processing circuitry is further configured to visually emphasize a reduced image corresponding to the candidate image more than other reduced images.

10. The apparatus according to claim 7, wherein the selection condition is for selecting the plurality of medical images as positioning targets from among the plurality of extracted medical images.

11. The apparatus according to claim 1, wherein the image memory further stores a plurality of measurement results measured by a plurality of living body physical quantity measurement and monitoring apparatuses, the processing circuitry is further configured to extract the plurality of medical images and a plurality of list display target measurement results, and generate a list in which a plurality of reduced images respectively corresponding to the plurality of extracted medical images, and the extracted measurement results are arranged.

12. The apparatus according to claim 1, wherein the image memory stores each of the plurality of images in association with the apparatus type and in addition to a patient identifier, and the processing circuitry is further configured to extract the plurality of medical images associated with a patient identifier selected by a user from among the plurality of images stored in the image memory.

13. The apparatus according to claim 1, wherein the processing circuitry is further configured to arrange only a reduced image corresponding to the candidate image in the list.

14. The apparatus according to claim 1, further comprising a diseases memory to store an identifier of each of a plurality of diseases in association with a selection condition for the candidate image, wherein the processing circuitry is further configured to identify the candidate image from among the plurality of extracted medical images, based on a selection condition associated with an identifier of disease selected by a user.

15. The image observation apparatus according to claim 14, wherein the selection condition is for selecting a medical image suitable for observation of the disease.

16. The apparatus according to claim 14, wherein the image memory further stores a plurality of measurement results measured by a plurality of living body physical quantity measurement and monitoring apparatuses, the processing circuitry is further configured to extract the plurality of medical images and a plurality of list display target measurement results, and identify a measurement result that is more likely to be used from among the extracted measurement results based on a selection condition associated with an identifier of the disease selected by the user.

17. An image observation method, comprising:

extracting a plurality of medical images as a list display target from an image memory storing a plurality of images and a plurality of apparatus types in association with each other;

generating a list in which a plurality of selectable reduced images respectively corresponding to the plurality of extracted medical images are arranged in a matrix having a vertical axis and a horizontal axis, the horizontal and vertical axes being defined by a condition input via an input apparatus, wherein the plurality of reduced images are arranged each apparatus type in the list, and the list visually indicates a reduced image corresponding to a candidate image of the plurality of extracted medical images that is more likely to be used; and displaying the generated list.

18. A non-transitory computer-readable recording medium recorded with a program for causing a computer to perform a method comprising:

extracting a plurality of medical images as a list display target from an image memory storing a plurality of images and a plurality of apparatus types in association with each other;

generating a list in which a plurality of selectable reduced images respectively corresponding to the plurality of extracted medical images are arranged in a matrix having a vertical axis and a horizontal axis, the horizontal and vertical axes being defined by a condition input via an input apparatus, wherein the plurality of reduced images are arranged by each apparatus type in the list, and the list visually indicates reduced image corresponding to a candidate image of the plurality of extracted medical images that is more likely to be used; and displaying the generated list.

* * * * *